United States Patent [19]
Baumoel

[11] 3,987,674
[45] Oct. 26, 1976

[54] TRANSDUCER STRUCTURE AND SUPPORT FOR FLUID MEASURING DEVICE

[76] Inventor: Joseph Baumoel, 107 Columbia Drive, Jericho, Long Island, N.Y. 11753

[22] Filed: Jan. 3, 1975

[21] Appl. No.: 538,366

[52] U.S. Cl. .............................. 73/194 A; 73/560
[51] Int. Cl.² .......................................... G01F 1/66
[58] Field of Search ..................... 73/194 A, 53, 560

[56] References Cited
UNITED STATES PATENTS

| | | | |
|---|---|---|---|
| 2,844,961 | 7/1958 | Hedrich et al. | 73/194 A |
| 2,912,856 | 11/1959 | Kritz | 73/194 A |
| 3,237,453 | 3/1966 | Yamamoto et al. | 73/194 A |
| 3,575,050 | 4/1971 | Lynnworth | 73/194 A |
| 3,782,193 | 1/1974 | Meyer et al. | 73/181 |

FOREIGN PATENTS OR APPLICATIONS

| | | | |
|---|---|---|---|
| 151,053 | 7/1960 | U.S.S.R. | 73/194 A |
| 288,333 | 1/1971 | U.S.S.R. | 73/194 A |

Primary Examiner—Charles A. Ruehl
Attorney, Agent, or Firm—Ostrolenk, Faber, Gerb & Soffen

[57] ABSTRACT

Transducers are positioned on opposite sides of a fluid conduit and are longitudinally displaced from one another along the axis of the conduit. Each transducer contains a transmitting and receiving transducer element which produces output energy in a direction represented by a ray forming an angle to the axis of the flow conductor, such that the sine of the angle is equal to the ratio of the velocity of sound in the transducer body supporting the transducer crystal to the shear mode sound velocity in the conduit walls of the conduit conducting the fluid. The longitudinal spacing between the centers of the transducers on opposite sides of the conduit is such that it intercepts a sonic beam passing through the liquid. The sine of the angle of that beam passing through the fluid within the conduit and between the transducers makes with a line normal to the axis of the pipe, equals the ratio of the velocity of sound in the liquid to the pipe shear mode velocity of sound in the conduit. A novel mounting clamp and spacing strip is provided to automatically adjust the longitudinal spacing between the transducers and to ensure that the transducers can be securely clamped to the pipe without displacing the transducers during the clamp tightening process. The rear of the transducer crystals is covered with damping layers to damp out the trailing portions of the transmitted signal. The flow display computer associated with the transducers is arranged to count clock pulses during transmission upstream between the transducers and then during transmission downstream between the transducers. The difference in the number of pulses counted is then proportional to the velocity of the fluid within the conduit. The difference in pulse count may be previously compensated for by changes in the sonic beam angle due to possible changes in the liquid sound velocity so as to eliminate any dependence on sonic velocity in the resultant flow velocity computation.

14 Claims, 9 Drawing Figures

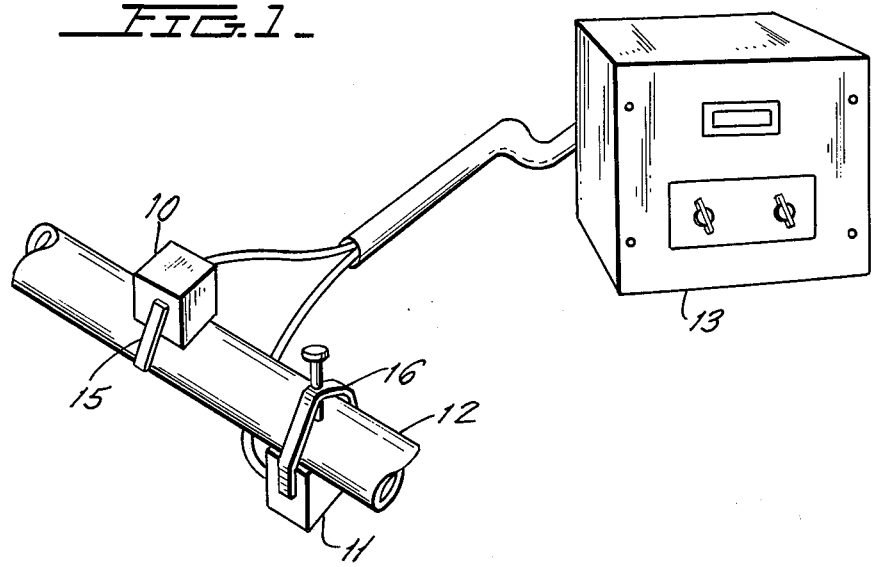
FIG. 1
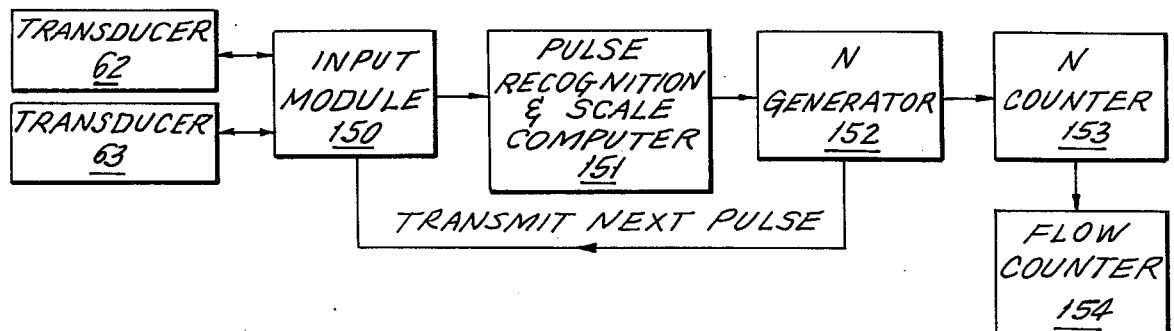
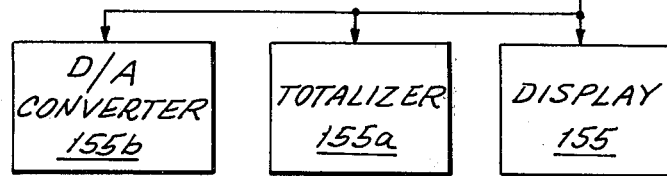
FIG. 6

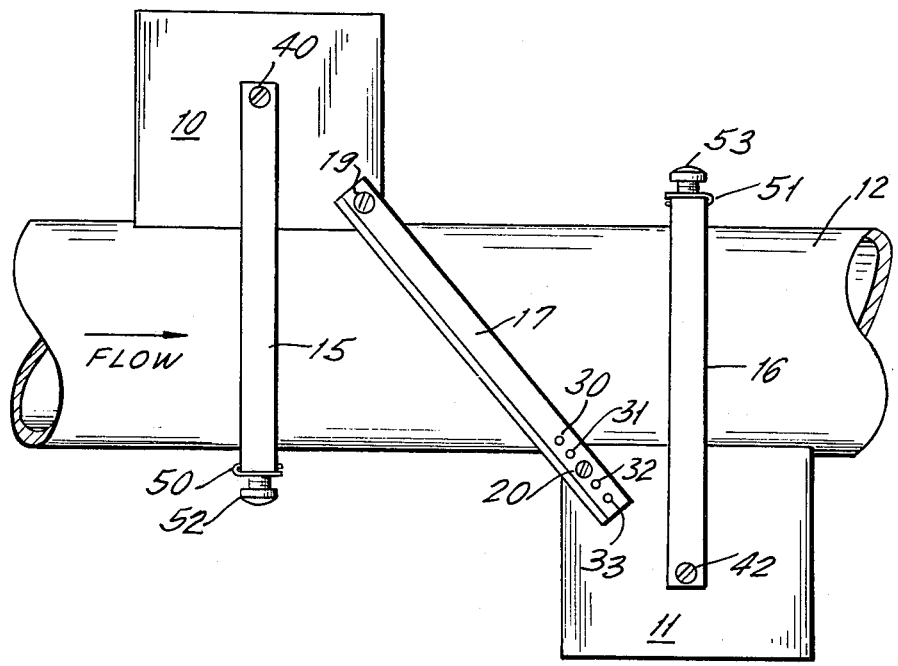
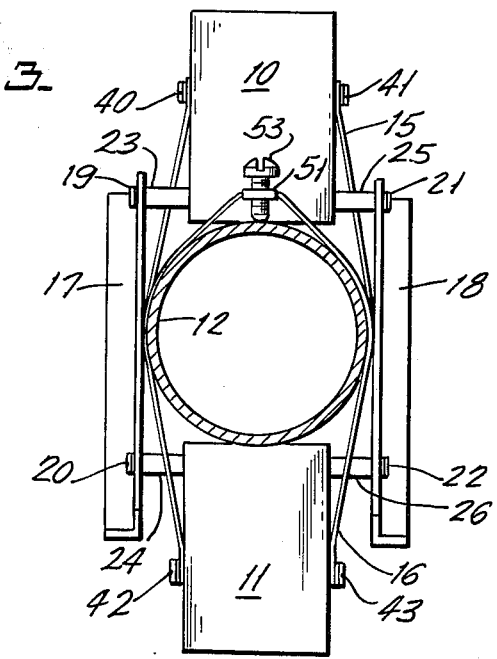

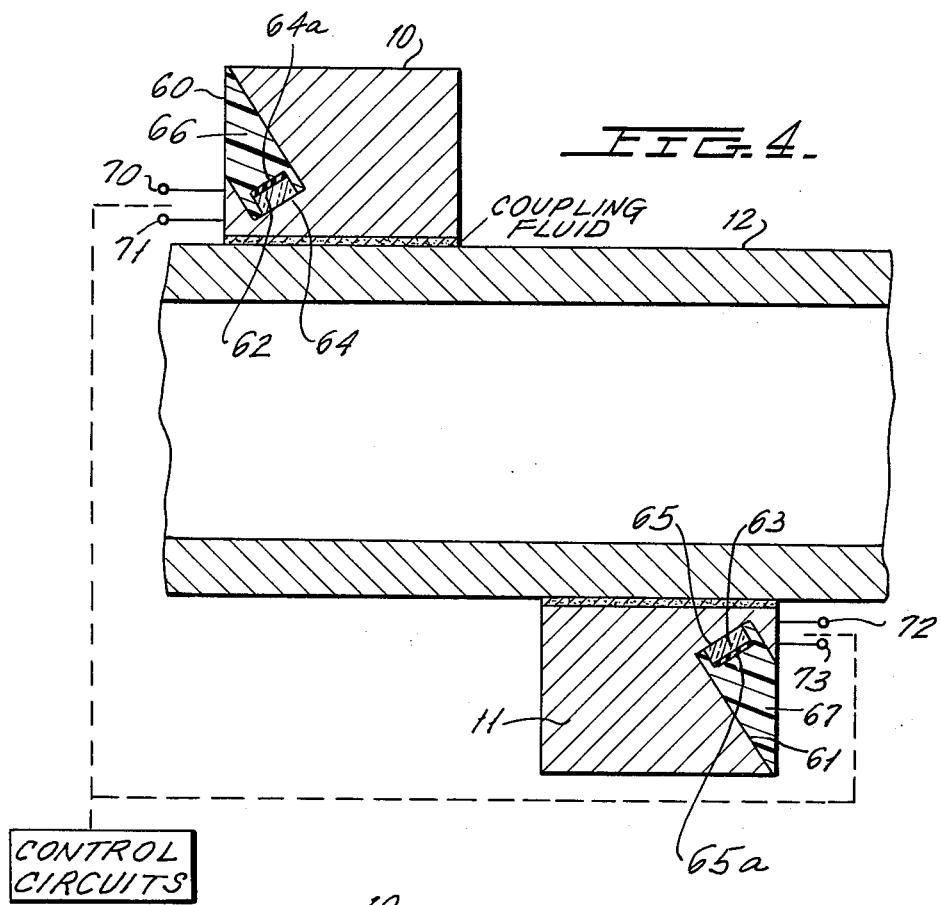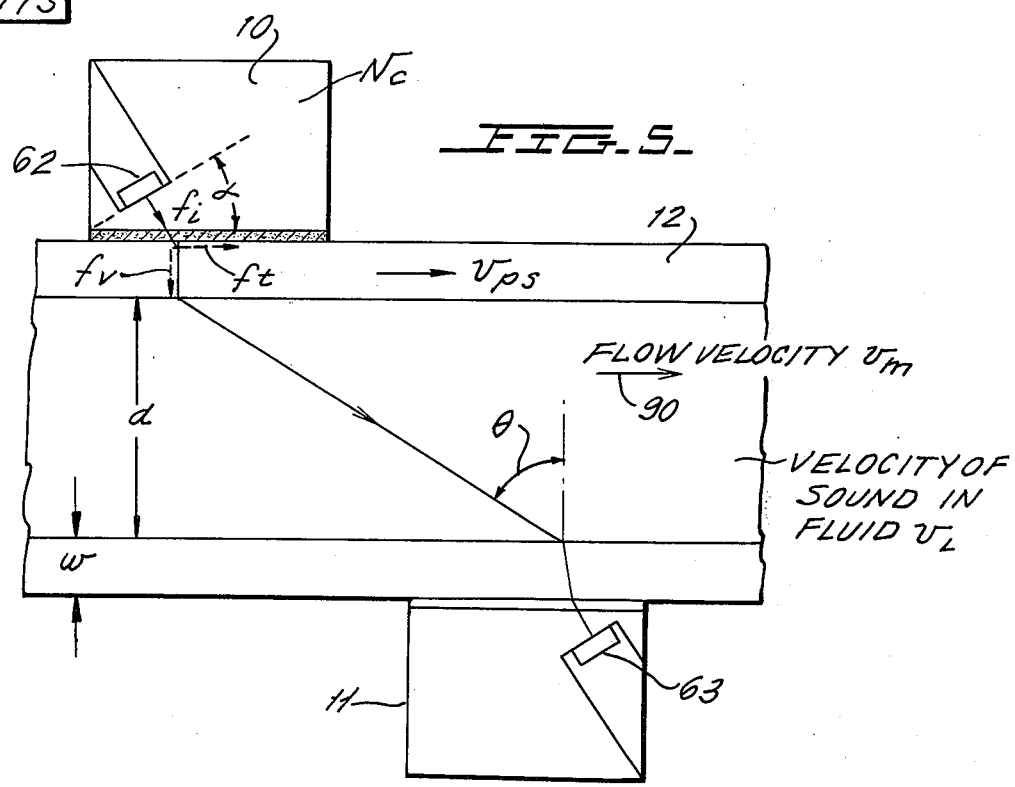

TRANSDUCER STRUCTURE AND SUPPORT FOR FLUID MEASURING DEVICE

RELATED APPLICATIONS

This application is related to copending application Ser. No. 326,089, filed Jan. 23, 1973, now U.S. Pat. No. 3,869,915, in the name of Joseph Baumoel, entitled DIGITAL FLOWMETER.

BACKGROUND OF THE INVENTION

This invention relates to a novel transducer construction and to a novel mounting arrangement for transducers which are used to monitor the condition of a fluid within a conduit, and more specifically relates to a novel transducer configuration which can be easily clamped onto the exterior of a fluid conduit for introducing sonic energy signals into the conduit which can be used to monitor or measure a condition of the fluid, such as its flow rate, and to deliver an electrical output and/or display related to the condition being monitored.

Flowmeters are generally well known to the art and many arrangements have been proposed in the past for monitoring a fluid condition within a conduit, such as a flow rate, by transducers mounted on the exterior of the conduit. By way of example, two transducers can be longitudinally spaced from one another on a fluid-carrying conduit and can be arranged to introduce ultrasonic signals into the pipe in both an upstream and a downstream direction and then compare the length of time taken for the signals to travel upstream and then downstream. The rate of flow of fluid in the conduit can be determined from the difference between the time taken for the signals to travel upstream or downstream.

The present invention provides a novel transducer configuration and spacing which maximizes the amount of signal which can be passed through the fluid and received by the receiving transducer, dependent upon the conduit material and size and the fluids being monitored and reliably controls the angle of the sonic beam passing through the liquid so that an accurate control of flowmeter calibration results.

BRIEF SUMMARY OF THE INVENTION

In accordance with an important feature of the invention, the angle of the conventional ray extending from the active transducer crystal surface toward the surface of the conduit to which it is coupled forms an angle to the axis of the conduit and thus to the conduit longitudinal axis, such that the phase velocity of the transducer wave along the longitudinal outer surface of the conduit is equal to the shear mode velocity of sound in the conduit along its longitudinal direction. This condition is achieved by causing the sine of the angle of the ray from the transducer to be equal to the ratio of the velocity of shear sound in the transducer body to the velocity of the sonic shear mode of the particular conduit to be sensed. When this condition is met, it has been found to increase the amount of signal which is transmitted through the liquid and received by the receiving transducer and also to minimize signal dispersion.

After recognizing that the angle of propagation of sound through the fluid being monitored (on which the flowmeter calibration depends) is such that the sine of the angle is proportional to the ratio of the velocity of sound in the fluid to the shear velocity of sound in the conduit, it becomes possible to count and/or predict flowmeter calibration without requiring an actual liquid flow calibration (a costly operation), merely by measuring the easily determined sonic velocities. Furthermore, it becomes possible to design computing circuits which automatically compensate for variation of sonic velocity over the full range of velocities possible for all liquids. Thus the flowmeter can be manufactured for accurate flow calibration knowing only the easily determined pipe shear mode velocity and without requiring actual liquid flow for calibration.

As a further important feature of the invention, a novel clamping arrangement is provided for clamping the transducers to the outer surface of the conduit on which they are mounted, with the spacing between the transducers being fixed by a novel spacing bar which extends between the transducers to assure proper transducer location. Furthermore, individual clamping straps are provided which can be tightened or spring loaded without interfering with the angular adjustment of the transducers on the conduit.

In designing the transducer structure, an active element will have an active plane surface which faces the conduit to be monitored and a transducer housing of a suitable plastic material or other material houses the active element and locates it relative to the conduit when the transducer assembly is clamped to the conduit. The material of the transducer housing will be such that the longitudinal speed of sound in the material is lower than the shear mode velocity of sound in the conduit wall. As an alternative the active element may face in the direction of the main conduit axis and utilize a coupling material of identical sonic velocity as the conduit — providing the active element vibrates in the shear mode itself. Preferably, the active element surface which is opposite to this plane surface, and thus is the active element rear surface, is covered with a damping layer which may be cork, or the like. This damping layer is advantageous in that it sharply damps the trailing portion of the transmitted ultrasonic energy signal and makes it easier for the receiving circuits to locate a given point in a complex return signal by reducing redundant noise which lowers the signal-to-noise ratio.

BRIEF DESCRIPTION OF THE DRAWINGS

FIG. 1 shows the transducer of the invention clamped to a fluid pipe or conduit and further shows the housing which contains the electronics for producing and for processing ultrasonic signals in the measurement system.

FIG. 2 is a side plan view of the transducers of FIG. 1 clamped to their conduit and particularly illustrates the novel clamping structure of the invention.

FIG. 3 is an end view of FIG. 2.

FIG. 4 is a cross-sectional view of the transducers and conduits of FIGS. 2 and 3.

FIG. 5 is similar to FIG. 4 but illustrates the direction taken by schematic rays of energy produced by and received by the transducers.

FIG. 6 schematically illustrates in block diagram a processing circuit which can be used for the production and processing of the ultrasonic signals in the measuring system.

DETAILED DESCRIPTION OF THE DRAWINGS

Figure 7:
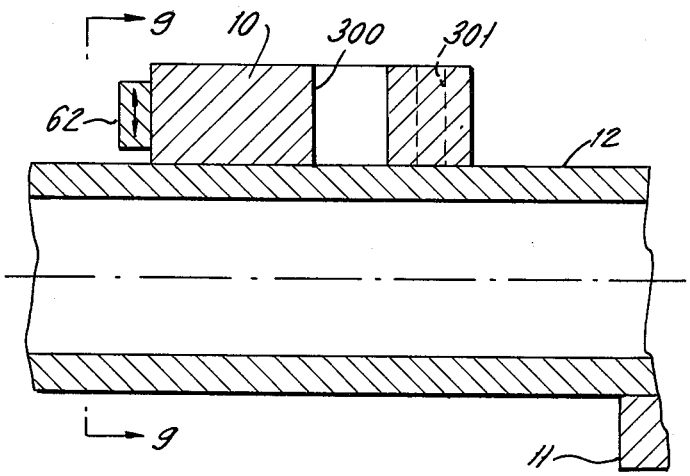
FIG. 7 is a longitudinal cross-sectional view, similar to FIG. 4, of a preferred embodiment of the invention.

Referring first to FIG. 1, there is schematically illustrated two transducers 10 and 11 which are clamped onto a hollow conduit or pipe 12. Conduit 12 may be of any desired material such as steel, plastic, concrete, or the like, of any given and known wall thickness and which is to contain or conduct any desired fluid, such as water, oil, or the like.

The arrangement of transducers 10 and 11 is provided in order to detect and monitor the flow or presence of fluid within the conduit 12. Conduit 12 may have a diameter, typically, from ½ inch to 60 inches, and any desired wall thickness.

Transducers 10 and 11 are clamped on opposite sides of the exterior diameter of pipe 12 by the clamping straps 15 and 16 (FIGS. 1, 2 and 3). The transducers 10 and 11 will be longitudinally spaced from one another by an optimum distance which will be later described, and which is dependent upon the velocity of sound in the liquid in the conduit 12 and the velocity of sound in the conduit material.

In order to space the transducers 10 and 11 by some fixed longitudinal distance, novel spacer bars 17 and 18 (FIGS. 2 and 3) are provided and are secured to transducers 10 and 11 by screws 19–20 for spacer bar 17, and screws 21–22 for the spacer bar 18.

As best shown in FIG. 3, the screws 19 to 22 may receive suitable cylindrical spacers 23 to 26, respectively, which extend between spacer bars 17 and 18 and the outer surfaces of transducer housings 10 and 11. The screws 19 to 22 are threadably received by suitable tapped openings (not shown) in the transducer housings 10 and 11.

In order to enable ready adjustment of the longitudinal spacing for different liquids along the center line of conduit 12 between transducers 10 and 11, a plurality of openings are provided in each of the spacer bars 17 and 18. These are shown for spacer bar 17 in FIG. 2 as the plurality of openings 30 to 33 which extend on either side of the opening receiving screw 20.

In order to securely clamp the transducers 10 and 11 to the pipe 12, metal pipe straps 15 and 16 have their opposite ends connected to transducers 10 and 11 by screws 40–41 and 42–43, respectively, which are threadably received by suitable tapped openings (not shown) in the transducer housings 10 and 11.

In order to securely tighten the clamping straps, the center of each strap receives a screw thread receiving element shown as screw thread receiving clips 50 and 51 for clamping bands 15 and 16, respectively, in FIGS. 2 and 3 which, in turn, receive clamping screws 52 and 53, respectively. This clamping arrangement then enables the transducers 10 and 11 to be securely clamped to the pipe with a longitudinal spacing determined by spacer bars 17 and 18 after the assembly is loosely mounted upon the pipe 12. Note that a conventional coupling fluid or grease of any desired type should be installed between transducers 10 and 11 and the outer diameter of pipe 12 which receives the transducers to ensure the effective coupling of sound energy between the transducers and the pipe wall.

With the arrangement shown in FIGS. 2 and 3, the tightening of screws 52 and 53 pulls the straps 15 and 16, respectively, evenly on their both sides to ensure that the transducers will be securely clamped without any rotation of the transducer bodies during the tightening process. Note further that transducers 10 and 11 may have small cylindrical channels in their bottoms which tend to conform to the curvature of the pipe 12 at the region where the transducers 10 and 11 engage the outer surface of pipe 12.

FIG. 4 is a cross-sectional view through the transducers 10 and 11 and the pipe 12 to which they are coupled and generally shows the construction of the transducers 10 and 11. Transducer housings 10 and 11 are generally identical to one another and consist of prisms of any desired material, such as nylon, or the like, which have good sound transmission qualities. The longitudinal velocity of sound in the housings 10 and 11 is lower than the shear mode velocity of sound in the wall of pipe 12. Channels 60 and 61 are formed in housings 10 and 11, and receive active transducer "crystals" 62 and 63, respectively. Active transducer members 62 and 63 may be of any desired type, such as barium titanate ceramic elements, or the like, and are generally flat members having active flat faces which face the outer surface of conduit or pipe 12, and are arranged to produce ultrasonic energy in pulse form in a direction perpendicular to the bases 64 and 65 of slots 60 and 61, respectively. The channels 60 and 61 are then encapsulated with any suitable plastic encapsulating material shown as encapsulating masses 66 and 67, respectively.

Transducer elements 62 and 63 are then provided with terminals 70–71 and 72–73, respectively, which are electrically connected to electronic control system 13, which will produce and receive and process ultrasonic signals associated with transducer elements 62 and 63, respectively.

An important feature of this invention is to cover the rear surfaces of elements 64 and 65 with layers of sound-absorbing materials 64a and 65a (FIG. 4), such as cork, sandpaper, and the like. This layer has been found to substantially eliminate and dampen the trailing portions of the transducer return signal, thereby to simplify the return signal characteristic and to allow improved signal processing.

FIG. 5 schematically illustrates the arrangement of FIG. 4 and further shows a typical ray of ultrasonic sound. It has been found that a particular transducer spacing should be used, and a particular angle at which the transducer elements 62 and 63 should be mounted relative to the axis of pipe 12 should be used in order to obtain unexpected optimum performance of the transducer arrangement such that a maximum ratio of liquid-received signal to pipe-received signal is obtained.

These critical parameters are analyzed as follows:

In the system of FIG. 5, the conduit 12 has a diameter $d$, and a wall thickness $w$, and the transducer housings 10 and 11 are of a material which has a speed of sound $v_c$ which could, for example, be $90 \times 10^3$ inches per second. In FIG. 5, it is presumed that the interior of conduit 12 is filled with a fluid flowing in the direction of arrow 90 where the speed of sound in the fluid has a velocity $v_L$.

The two crystals 62 and 63 are then mounted with their flat energy producing faces (adjacent surfaces 64 and 65) forming an angle $\alpha$ to the axis of conduit 12. Transducer bodies 10 and 11 are so mounted that a ray representing sound through the fluid in the interior of tube 12 is at an angle $\Theta$ to a line normal to the center line of conduit 12.

In FIG. 5, there is also shown a generalized ray $f_i$ which is produced by crystal 62 and which is resolved into its shear and longitudinal components $f_v$ and $f_t$ when it enters the wall of conduit 12. Note that ray $f_i$ is but one of a band of parallel rays which extend over the full active surface of transducer 62 which sequentially intersect the surface of pipe 12 at a given phase velocity along the pipe surface. Ray $f_v$ is refracted as it enters the fluid within conduit 12 at an angle $\Theta$ and it then reenters the wall of tube 12 on the opposite side of the tube to ultimately reach transducer crystal 63.

In accordance with an important feature of the invention, the angle $\alpha$ is chosen so that the phase velocity of the normal component $f_v$ of the incident wave in the pipe wall is equal to the velocity $v_{ps}$ of a pipe shear mode vibration, characteristic for the conduit 12 of a given wall thickness and material.

Since the normal component $f_v$ excites the shear mode in the pipe, matching the phase velocity of the incident wave $f_i$ as its wave front reaches the outer diameter of conduit 12, it causes the amplitude of the shear mode vibration in the conduit 12 to increase to a peak value as the beam moves toward the right in FIG. 5. Note that the longitudinal portion $f_t$ of the incident wave $f_i$ cannot pass into the liquid within conduit 12 since it is a shear wave to the liquid at the inside of the conduit wall. As well known, liquids cannot sustain shear mode ultrasonic transmission. However, the pipe shear vibration component is perpendicular to the liquid interface and passes readily into the liquid as a longitudinal liquid wave.

In order to ensure matching of the transducer longitudinal mode phase velocity to the pipe shear mode velocity, $v_{ps}$, the angle $\alpha$ is designed such that:

$$\sin \alpha = \frac{v_c}{v_{ps}} \qquad (1)$$

Thus the incident wave from transducer 62 will travel through transducer housing 10 at a speed $v_c$ and its wave front will intersect the outer diameter of conduit 12 at the velocity $v_{ps}$ which is equal to the velocity of sound in the pipe wall 12.

It can now be understood that since the velocity of sound in the liquid $v_L$ is normally much less than the shear mode velocity of sound in the pipe wall $v_{ps}$ that, for practical angles of $\alpha$, the transducer housings 10 and 11 should be of material having sound velocities somewhat less than $v_{ps}$. Typically, housings 10 and 11 may be made of nylon.

The resonant frequency of transducer elements 62 and 63 is chosen with regard to the longitudinal pipe velocity $v_{pL}$ and in conjunction with the pipe wall thickness $w$ so as to avoid interference effects due to reflection of the normal wave $f_v$ from the inside surface of the pipe wall which could cause cancellation of incident waves at the pipe transducer interface. The designer should also take into account the attenuation of sound and liquids which is a function of frequency and of the size of solid particles which might be present in the liquid in the conduit 12. Generally, the most useful frequencies will range from 100 kilohertz to 10 megahertz. Angles $\Theta$ and $\alpha$ may range from 15° to 50° and from 20° to 90°, respectively.

In a specific embodiment of the invention, and where a steel walled pipe is used, it has been found advantageous to use steel for the transducer bodies 10 and 11 and to make the angle $\alpha$ equal to 90°. In this embodiment, the transducers transmit energy in the direction of the pipe axis and a shear mode velocity is induced in the pipe wall. This specific matching of transducer and pipe materials thus leads to great structural simplification since there is an automatic match of phase velocity and shear mode velocity in the pipe.

Since the sound travels at right angles to the pipe diameter, by Snell's law:

$$\frac{\sin \theta}{v_L} = \frac{\sin 90°}{v_{ps}} \text{ or}$$

$$\sin \theta = \frac{v_L}{v_{ps}} \qquad (2)$$

That is, in FIG. 5, as energy travels from left to right in the conduit 12 at velocity $v_{ps}$, it radiates into the liquid and within conduit 12 at the angle $\Theta$. Energy from the transducer crystal 62 travels over a band of some thickness, through the liquid and to the transducer crystal 63. The amplitude of the instantaneous signals within this band is small at its left and right-hand ends, and is maximum at its center. Only by spacing transducer crystals 62 and 63 by an appropriate distance does one ensure that one receives the greatest total energy from the other.

Thus, in the design of the transducer arrangement and by knowing the material of the conduit 12 and thus $v_{ps}$ and the fluid being monitored, and thus $v_L$ and by knowing the diameter $d$ of conduit 12, one can accurately locate transducers 10 and 11 longitudinally with respect to one another and to optimize their positions so that they will transmit and receive maximum amounts of energy from one another.

Noting that the sin $\Theta$ is equal to $v_L/v_{ps}$, the measurement of the velocity of flow $v_m$ within conduit 12 becomes substantially simplified. More specifically, the flow display computer will display a reading obtained by permitting a counter to count clock pulses in an arbitrarily chosen positive direction during N cycles of "up" transmit pulses, and in a negative direction for an equal number of N "down" transmit pulses. Thus, at the end of N up-down cycles, the residue in the counter will be proportional to N times the difference in "up" versus "down" transmit times multiplied by clock frequency times a constant. Thus, $$F = N \, m \, f_c \, \Delta T \qquad (3)$$

where $N$ is a selected number of up and down transmit pulses,
$m$ is a proportionality factor,
$f_c$ is the clock frequency, and
$\Delta T$ is the difference between transmission upstream and downstream due to the flow of fluid within the conduit at some liquid velocity $v_m$.

It can also be shown that:

$$\Delta T = \frac{v_m}{v_L} \sin \theta \left( \frac{d}{v_L \cos \theta} \right) \qquad (4)$$

However, since sin $\Theta$ equals $v_L/v_{ps}$, then $$\Delta T = \frac{v_m}{v_{ps}} \left( \frac{d}{v_L \cos \theta} \right) \qquad (5)$$

It will be noted that the actual time that the ultrasonic energy is in the liquid within conduit 12, as contrasted to the walls of conduit 12 and the actual transducer bodies 10 and 11 can be stated as:

$$T_L = \frac{d}{v_L \cos \theta} \quad (6)$$

Therefore, the quantity to be measured which is related to flow rate is:

$$F = m f_c \frac{v_m}{v_{ps}} \times T_L \quad (7)$$

By making $m = k/T_L$, the flow reading in numbers of pulses counted is proportional to the constants $k, f_c$ and $l/v_{ps}$ and is directly proportional to the quantity to be measured $v_m$.

By appropriate choice of the constant $k$, the reading F can be made proportional to flow in any desired unit such as gallons per minute, gallons per hour, or the like. It is also possible, if desired, through the use of appropriate circuits to create a pulse rate $P_{gen}$ which will be proportional to flow rate rather than to the count F of equation (7). In this case, the multiplier "$k$" for $P_{gen}$ can be made inversely proportional to $T_L$ so as to result in a pulse rate proportional only to flow and not a function of $T_L$ or $v_L$ as in the case of equation (7), whereby:

$$P_{gen} = \frac{k v_m}{v_{ps}} \quad (8)$$

The novel transducer arrangement of FIGS. 1 to 5 can be operated in connection with any desired type of electronics signal processing arrangement which is used for the production of ultrasonic energy pulses and for the measurement of the difference in transmission times of these pulses upstream and downstream within the conduit 12 in order to measure the flow rate of fluid within the conduit. In general, the arrangement set forth in copending application Ser. No. 326,089, referred to above, can be directly adopted.

In general, the electronics system can be the system set forth in schematic fashion in FIG. 6.

The generalized circuits of FIG. 6 drive and are driven by transducers 62 and 63 and include an input module 150, a scale computer 151, an N generator circuit 152, an N counter circuit 153, a flow counter 154 and a display and/or control module 155. The display 155 may further be coupled to drive a digital-to-analog converter 155b and a flow totalizer 155a.

The flow computer circuitry and structure of the blocks 150 to 155 of FIG. 6 will be contained in the housing 13 in FIGS. 1 to 4.

The basic purpose of input module 150 is to generate a "transmit signal" which is selectively applied to transducer 62 or 63 to generate the desired acoustic signal either in an upstream or downstream direction. The effect of fluid flow in the conduit 12 will increase or reduce the transmit time of the acoustical signal in the down and upstream directions, respectively. Input module 150 also receives and amplifies the signal received by the transducer which is not transmitting, and applies this received signal to the scale computer 151.

Scale computer 151 has several functions which include:

a. The recognition of a proper transducer return signal and the rejection of unwanted noise signals, such as the transducer transmit signal which propagates through the pipe wall.

b. The recognition of a given point in the transducer return signal to measure the transmission time for the first pulse in a given direction in a series of N pulse cycles, and to serve as the standard for the remaining N pulses of the cycle in the same direction. By using layers 64a and 65a on the rear surfaces of transducer elements 62 and 63, the trailing edge of the return signal is sharply damped to simplify the recognition of the given point.

c. Circuits which automatically determine the refractive angle $\theta$ of sound transmission through the liquid to automatically compensate the readout for effects of different refraction angle in liquids having different sound velocities.

d. Circuits which can adjust operation of the controls for varying pipe size and material so that all other modules are usable for all pipe sizes.

N generator 152 generally operates to serve the following functions:

a. The N generator produces the "N" pulses which start each counting cycle and each transmit signal.

b. A pulse counting circuit is provided to measure and memorize the pulse transmission time of a first N cycle and as the standard for the pulse transmission time of succeeding N pulses in a given up or down cycle sequence. This ensures that all of a given group of up or down cycles are referred to the same point in the complex signal return pattern. This makes the system less sensitive to "jitter" or amplitude variation in the return signal caused by factors such as fluid turbulence and the like.

The N counter 153 operates to serve the following functions:

a. It provides circuitry to "start-up" the system by causing the generation of a transmit pulse if N pulses are not received from the N generator for a given length of time.

b. Circuits are provided to count the number of N cycles in a count cycle and to cause the number of count cycles per read cycle to fall within a given preferred range of between 128 and 512.

c. It contains many timing logic circuits for the system.

d. It contains the circuitry which switches the mode of operation of the system from a transmit upstream condition to a transmit downstream condition.

e. It provides timing delay circuits to delay the initiation of a next count-up, count-down or read cycle for a short delay period.

Flow counter 154 has the major purpose of accumulating clock pulses in an up-down counter by adding pulses during up cycles, and subtracting pulses during down cycles of a clock gate. Counter 154 has a storage register which receives the pulse residue of the up-down counter at the end of a read cycle. Pulses are accumulated in the storage register, for example, from 0.2 to 5 seconds and this stored reading is displayed to represent the average flow rate during the previous read cycle.

The output of the stored reading in flow counter 154 is applied to display 155, which indicates a constantly updated flow display at the end of each read cycle. Readings may also be accumulated in a totalizer 155a after being multiplied by elapsed time to give a count proportional to total flow in, for example, gallons. This total flow could be displayed typically in a six digit electromechanical counter.

A digital-to-analog converter 155b is provided to convert the flow signal to an analog d–c signal proportional to flow which can, in turn, be used for flow control purposes. This voltage output could also operate an analog display with a high-low alarm relay device.

Figure 8:
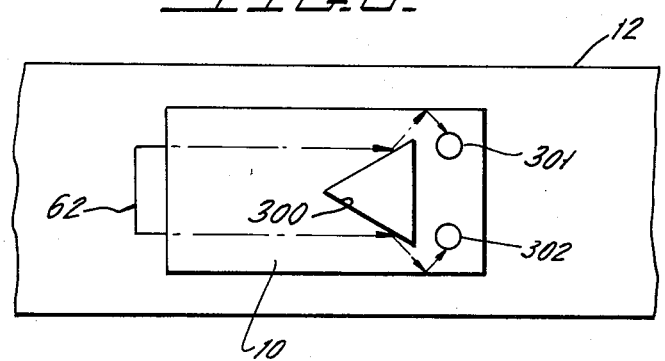
FIG. 8 is a top plan view of FIG. 7.
Figure 9:
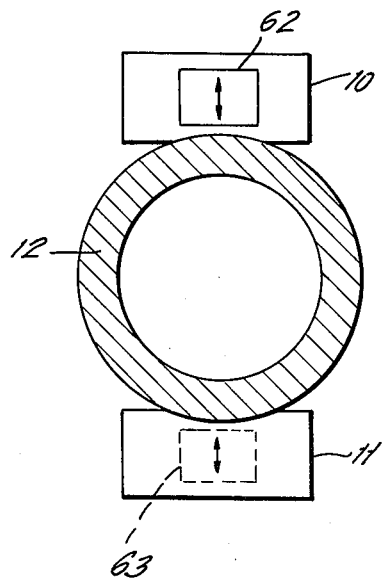
FIG. 9 is a cross-sectional view of FIG. 7 taken across section line 9—9 in FIG. 7.

FIGS. 6 to 9 show an embodiment of the invention wherein the angle α (FIG. 5) is 90°, and wherein the material of the transducer housings 10 and 11 is the same as the material of conduit 12. Thus, if the conduit 12 is of steel, housings 10 and 11 are also of steel. The transducer elements 62 are then arranged to vibrate in a direction perpendicular to the axis of pipe 12, thereby to introduce a shear-mode wave which propagates axially along the transducers 10 and 11, and axially along the pipe wall of conduit 12. Note that by making α equal to 90°, that there is an automatic match of phase velocity and shear mode velocity when the transducer housings and conduit are of the same material.

As a further feature of the invention, and to prevent interference from signals reflected from the rear wall of transducer housing 10 (or 11), the transducer may have internal baffles, shown by the triangular cut-out 300, and circular cut-outs 301 and 302 (FIGS. 7 and 8), which tend to absorb and deflect shear mode waves traveling to the rear surface of transducer housing 10, as shown by the arrows. The novel cut-out baffles significantly prevent signals from being internally reflected from the rear surface of transducer housing 10 (or 11), which could be mistaken for a delayed signal from the transducer.

Although there has been described a preferred embodiment of this invention, many variations and modifications will now be apparent to those skilled in the art. Therefore, this invention will be limited, not by the specific disclosure herein, but only by the appended claims.

The embodiments of the invention in which an exlusive privilege or property is claimed are defined as follows:

1. Ultrasonic monitoring means for monitoring a given parameter of the fluid within a sealed, elongated hollow conduit; said monitoring means comprising first and second transducer means each secured to the outer surface of said conduit and being longitudinally spaced from one another along the length of said conduit; a coupling fluid disposed between each of said first and second transducer means and said outer surface of said conduit; electronic circuit means connected to said first and second transducer means for initiating pulses of ultrasonic energy from said first, and then from said second transducer means, which pulses pass through the fluid within said hollow conduit, and for measuring the time taken for said pulses to travel from said first to said second transducer means and from said second to said first transducer means, and to indicate, from said measurement, said given parameter of said fluid; said first and second transducer means each comprising first and second respective transducer elements having respective active plane surfaces, and first and second transducer housing means supporting said first and second transducer elements respectively, and coupling ultrasonic energy from said active plane surfaces of said first and second transducer elements to said outer surface of said conduit; the sine of the angle beetweeen said plane surfaces of said first and second transducer elements and the axis of said conduit being equal to the ratio between the velocity of sound in said first and second transducer housing means to the shear mode velocity of sound in the wall of said conduit.

2. The monitoring means of claim 1 wherein the parameter measured is fluid flow, and wherein the flow measured is related to the time difference measured between the time taken for ultrasonic energy to travel upstream and downstream between said first and second transducer elements.

3. The monitoring means of claim 2 wherein said time difference is related to a pulse count difference.

4. The monitoring means of claim 1 wherein said first and second transducer means are mounted on opposite sides of said conduit.

5. Ultrasonic monitoring means for monitoring a given parameter of the fluid within a sealed, elongated hollow conduit; said monitoring means comprising first and second transducer means each secured to the outer surface of said conduit and being longitudinally spaced from one another along the length of said conduit; a coupling fluid disposed between each of said first and second transducer means and said outer surface of said conduit; electronic circuit means connected to said first and second transducer means for initiating pulses of ultrasonic energy from said first, and then from said second transducer means, which pulses pass through the fluid within said hollow conduit, and for measuring the time taken for said pulses to travel from said first to said second transducer means and from said second to said first transducer means, and to indicate, from said measurement, said given parameter of said fluid; said first and second transducer means each comprising first and second respective transducer elements having respective active plane surfaces and first and second transducer housing means supporting said first and second transducer elements respectively, and coupling ultrasonic energy from said active plane surfaces of said first and second transducer elements to said outer surface of said conduit; the sine of the angle of a ray of ultrasonic energy from the center of said first transducer element to the center of said second transducer element as measured against a normal to the axis of said conduit being equal to the ratio between velocity of sound in said fluid to the shear mode velocity of sound in the wall of said conduit.

6. The monitoring means of claim 5 wherein said first and second transducer means are mounted on opposite sides of said conduit and including first and second clamping means extending from said first and second transducer means respectively and around said conduit for clamping said first and second transducer means to said conduit, and spacer bar means disposed diagonally across said conduit and fixed at its ends to said first and second transducer housing means, thereby to fix the longitudinal spacing between said first and second transducer housings.

7. The monitoring means of claim 5 wherein the velocity of sound in said first and second transducer housing means is lower than the shear mode velocity of sound in the wall of said conduit.

8. Ultrasonic monitoring means for monitoring a given parameter of the fluid within a sealed, elongated hollow conduit; said monitoring means comprising first and second transducer means each secured to the outer surface of said conduit and being longitudinally spaced from one another along the length of said conduit; electronic circuit means connected to said first and second transducer means for initiating pulses of ultrasonic energy from said first, and then from said second transducer means, which pulses pass through the fluid within said hollow conduit, and for measuring the time taken for said pulses to travel from said first to said second transducer means and from said second to said first transducer means, and to indicate, from said measurement, said given parameter of said fluid; said first and second transducer means each comprising first and second respective transducer elements having respective active plane surfaces which are perpendicular to the axis of said conduit, and first and second transducer housing means supporting said first and second transducer elements respectively, and coupling the shear wave mode of energy from said active plane surfaces of said first and second transducer elements into said outer surface of said conduit; said first and second transducer housing means being of a material identical to the material of said conduit.

9. The monitoring means of claim 8 wherein the parameter measured is fluid flow, and wherein the flow measured is related to the time difference measured between the time taken for ultrasonic energy to travel upstream and downstream between said first and second transducer elements.

10. Ultrasonic monitoring means for monitoring a given parameter of the fluid within a sealed, elongated hollow conduit; said monitoring means comprising first and second transducer means each secured to the outer surface of said conduit and being longitudinally spaced from one another along the length of said conduit; a coupling fluid disposed between each of said first and second transducer means and said outer surface of said conduit; electronic circuit means connected to said first and second transducer means for initiating pulses of ultrasonic energy from said first, and then from said second transducer means, which pulses pass through the fluid within said hollow conduit, and for measuring the time taken for said pulses to travel from said first to said second transducer means and from said second to said first transducer means, and to indicate, from said measurement, said given parameter of said fluid; said first and second transducer means each comprising first and second respective transducer elements having respective active plane surfaces, and first and second transducer housing means supporting said first and second transducer elements respectively, and coupling said active plane surfaces of said first and second transducer elements to said outer surface of said conduit; the sine of the angle between said plane surfaces of said first and second transducer elements and the axis of said conduit being equal to the ratio between the velocity of sound in said first and second transducer housing means to the velocity of sound in the wall of said conduit; and a layer of sound absorbing material disposed between the surface of said first and second transducer elements opposite their said active plane surfaces and said first and second transducer housings respectively.

11. Ultrasonic monitoring means for monitoring a given parameter of the fluid within a sealed, elongated hollow conduit; said monitoring means comprising first and second transducer means each secured to the outer surface of said conduit and being longitudinally spaced from one another along the length of said conduit; electronic circuit means connected to said first and second transducer means for initiating pulses of ultrasonic energy from said first, and then from said second transducer means, which pulses pass through the fluid within said hollow conduit, and for measuring the time taken for said pulses to travel from said first to said second transducer means and from said second to said first transducer means, and to indicate, from said measurement, said given parameter of said fluid; said first and second transducer means each comprising first and second respective transducer elements having respective active plane surfaces, and first and second transducer housing means supporting said first and second transducer elements respectively, and coupling said active plane surfaces of said first and second transducer elements to said outer surface of said conduit; openings formed in said first and second transducer housing means to deflect ultrasonic energy before it reaches the rear surface of said housing, and a layer of sound absorbing material disposed between the surface of said first and second transducer elements opposite to their said active plane surfaces and said first and second transducer housings respectively.

12. Ultrasonic monitoring means for monitoring a given parameter of the fluid within a sealed, elongated hollow conduit; said monitoring means comprising first and second transducer means each secured to the outer surface of said conduit and being longitudinally spaced from one another along the length of said conduit; a coupling fluid disposed between each of said first and second transducer means and said outer surface of said conduit; electronic circuit means connected to said first and second transducer means for initiating pulses of ultrasonic energy from said first, and then from said second transducer means, which pulses pass through the fluid within said hollow conduit, and for measuring the time taken for said pulses to travel from said first to said second transducer means and from said second to said first transducer means, and to indicate, from said measurement, said given parameter of said fluid; said first and second transducer means each comprising first and second respective transducer elements having respective active plane surfaces, and first and second transducer housing means supporting said first and second transducer elements respectively, and coupling said active plane surfaces of said first and second transducer elements to said outer surface of said conduit; the sine of the angle between said plane surfaces of said first and second transducer elements and the axis of said conduit being equal to the ratio between the velocity of sound in said transducer housing to the velocity of sound in the wall of said conduit; openings formed in said first and second transducer housing means to deflect ultrasonic energy before it reaches the rear surface of said housing, and a layer of sound absorbing material disposed between the surface of said first and second transducer elements opposite to their said active plane surfaces and said first and second transducer housings respectively.

13. Ultrasonic monitoring means for monitoring a given parameter of the fluid within a sealed, elongated hollow conduit; said monitoring means comprising first and second transducer means each secured to the outer surface of said conduit and being longitudinally spaced from one another along the length of said conduit; electronic circuit means connected to said first and sescond transducer means for initiating pulses of ultrasonic energy from said first, and then from said second transducer means, which pulses pass through the fluid within said hollow conduit, and for measuring the time taken for said pulses to travel from said first to said second transducer means and from said second to said first transducer means, and to indicate, from said measurement, said given parameter of said fluid; said first and second transducer means each comprising first and second respective transducer elements having respective active plane surfaces, and first and second transducer housing means supporting said first and second transducer elements respectively, and coupling said active plane surfaces of said first and second transducer elements to said outer surface of said conduit; said first and second trasducer housing means being of a material having the same speed of sound as the material of the wall of said conduit; said active plane surfaces being at ninety degrees to said outer surfaces of said conduit.

14. The device of claim 13 wherein said first and second transducer housing means and said conduit are of steel.

* * * * *